(12) United States Patent
Imaizumi et al.

(10) Patent No.: US 7,415,144 B2
(45) Date of Patent: Aug. 19, 2008

(54) CELL OBSERVATION DEVICE AND CELL OBSERVATION METHOD

(75) Inventors: Yuji Imaizumi, Nagoya (JP); Yoshitaro Nakano, Shizuoka-ken (JP); Ichiro Sase, Kanagawa (JP)

(73) Assignee: Nikon Corporation, Tokyo (JP)

( * ) Notice: Subject to any disclaimer, the term of this patent is extended or adjusted under 35 U.S.C. 154(b) by 276 days.

(21) Appl. No.: 11/390,419

(22) Filed: Mar. 28, 2006

(65) Prior Publication Data

US 2006/0210962 A1 Sep. 21, 2006

Related U.S. Application Data

(63) Continuation of application No. PCT/JP2004/014212, filed on Sep. 29, 2004.

(30) Foreign Application Priority Data

Sep. 29, 2003 (JP) ............................. 2003-337859

(51) Int. Cl.
*G06K 9/00* (2006.01)

(52) U.S. Cl. .................. 382/128; 382/133; 702/19; 702/20; 702/21; 702/27; 435/4; 435/6; 435/29; 435/283.1; 356/36; 356/39

(58) Field of Classification Search ................ 382/128, 382/133; 702/19, 20, 21, 27; 707/3, 4, 6; 356/36, 39; 706/4, 5, 46; 435/4, 6, 29, 283.1, 435/287.2

See application file for complete search history.

(56) References Cited

U.S. PATENT DOCUMENTS 5,548,661 A * 8/1996 Price et al. .................. 382/133

5,989,835 A * 11/1999 Dunlay et al. .................. 506/10

(Continued)

FOREIGN PATENT DOCUMENTS

JP 6-138118 5/1994

(Continued)

OTHER PUBLICATIONS

Fibronectin controls capillary endothelial cell growth by modulating cell shape, Ingber et al., 1990.*
Endothelial Growth factors and extra cellular matrix regulate DNA synthesis through modulation of cell and nuclear expansion, Ingber et al, 1987.*
R. Weimer et al., "Characterization of centromere arrangements and test for random distribution in G0, G1, S, G2, G1, and early S' phase in human lymphocytes", *Human Genetics*, 88:673-682 (1992).

*Primary Examiner*—Andrew W. Johns
*Assistant Examiner*—Nancy Bitar
(74) *Attorney, Agent, or Firm*—Morgan, Lewis & Bockius LLP (57) ABSTRACT

The cell observation device and method aims to easily study the correlation between initial states of cells and their reactions without using a synchronous culture method. For this purpose, the cell observation device includes an image acquisition unit acquiring an image of a specimen including a plurality of cells; a stimulating unit applying a predetermined stimulation to the plural cells; a determining unit determining initial states of the plural cells from the image which is acquired by the image acquisition unit before the stimulating unit applies the stimulation; a finding unit finding reactions of the plural cells to the stimulation, from the image acquired by the image acquisition unit after the stimulating unit applies the stimulation; and a generating unit generating information on correlation between the initial states and the reactions of the plural cells.

8 Claims, 4 Drawing Sheets

U.S. PATENT DOCUMENTS

| | | | | |
|---|---|---|---|---|
| 6,103,479 | A * | 8/2000 | Taylor | 506/14 |
| 6,280,967 | B1 * | 8/2001 | Ransom et al. | 435/29 |
| 6,461,813 | B2 * | 10/2002 | Lorens | 506/10 |
| 6,558,916 | B2 * | 5/2003 | Veerapandian et al. | 435/29 |
| 6,897,031 | B1 * | 5/2005 | Fisher et al. | 435/7.21 |
| 6,999,607 | B2 * | 2/2006 | Kiros et al. | 382/128 |
| 2003/0134269 | A1 * | 7/2003 | Hirai et al. | 435/4 |
| 2003/0204316 | A1 * | 10/2003 | Dunlay et al. | 702/19 |
| 2006/0210962 | A1 * | 9/2006 | Imaizumi et al. | 435/4 |

FOREIGN PATENT DOCUMENTS

| | | |
|---|---|---|
| JP | 2002-512362 | 4/2002 |
| JP | 2002-218995 | 8/2002 |
| JP | 2002-355090 | 12/2002 |
| JP | 2003-500664 | 1/2003 |
| JP | 2003-506098 | 2/2003 |
| WO | 00/72258 | 11/2000 |

* cited by examiner

CELL OBSERVATION DEVICE AND CELL OBSERVATION METHOD

CROSS REFERENCE TO RELATED APPLICATION

This application is a continuation application of International Application PCT/JP 2004/14212, filed Sep. 29, 2004, designating the U.S., and claims the benefit of priority from Japanese Patent Application No. 2003-337859, filed on Sep. 29, 2003, the entire contents of which are incorporated herein by reference.

BACKGROUND OF THE INVENTION

1. Field of the Invention

The present invention relates to a cell observation device and a cell observation method for observing reactions of cells, and more particularly, to a cell observation device and the like suitable for screening in a development process of medicinal products.

2. Description of the Related Art

It is generally practiced to culture a large number of cells by using a known synchronous culture method (see, for example, Reference 1), to uniformalize states (for example, the timing of a mitotic phase of a cell cycle) of the large number of cells and observe reactions of the cells to stimulation such as the introduction of a drug. According to this method, an average reaction of the large number of cells can be observed.

Reference 1: R. Weimer, T. Haaf, J. Kruger, M. Poot, M. Schmid, "Characterization of centromere arrangements and test for random distribution in G0, G1, S, G2, G1, and early S' phase in human lymphocytes", Human Genetics 88:673-682 (1992)

However, the aforesaid synchronous culture method needs very complicated works. Further, in order to study the correlation between initial states (for example, states immediately before the stimulation is applied) of a large number of cells and their reactions, a large variety of specimens composed of cells in different initial states have to be prepared by the synchronous culture method, which requires enormous labor and time.

Here, an experiment conducted by the present inventors will be described. In this experiment, the correlation between the initial states of the large number of cells and their reactions was studied by the combination of conventional methods. First, a large variety of specimens are prepared by the synchronous culture method. Specifically, a cell suspension at a logarithmic growth phase is adjusted to a concentration of $5\times10^5$ cells/ml, a thymidine solution is added thereto so that the final concentration (different depending on the kind of the cells) becomes 0.5 to 2.5 mM, and the cells are cultured in a $CO_2$ incubator for 16 to 24 hours. This operation causes the large number of cells in the specimen to synchronize in a boundary of a gap phase (G1 phase)/a DNA synthesis phase (S phase) and in the S phase of a cell cycle. Next, cell culture supernatants (substances on the surface) are removed by centrifugal separation and are returned to a culture solution to be cultured for 15 hours. This operation causes the large number of cells in the specimen to enter the boundary of a gap phase (G2 phase)/a mitotic phase (M phase). Further, a thymidine solution is added so that the final concentration becomes 0.5 to 2.5 mM, and the cells are cultured for 16 to 24 hours in the $CO_2$ incubator. This operation causes the large number of cells in the specimen to synchronize in the boundary of the G1 phase/the S phase. Note that, in order to know in which phase of the cell cycle the large number of cells in the specimen are synchronized, a DNA amount of each of the cells may be measured by using a known flow cytometry after the cells are dyed with propidium iodidle (PI). The inventors of the present invention prepared a large variety of the specimens in different cell initial states (here, phases of the cell cycle) in the above-described manner.

Figure 4:
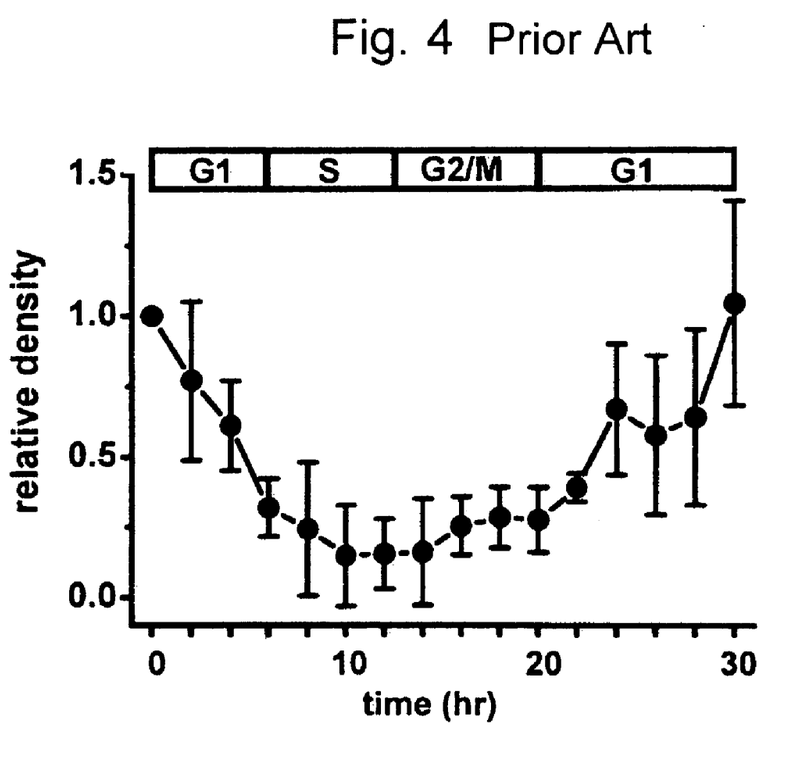
FIG. 4 is the result of study on the correlation between initial states of cells and their reactions, conducted by using a conventional method.

Then, an expression amount of ion channels on cell surfaces was measured in each of a large variety of the specimens. The ion channel is small conductance (SK) type 2 of calcium-activated potassium channels. A known Western blot method using anti-SK2 channel antibody was implemented for the measurement. FIG. 4 shows the measurement result. In FIG. 4, the horizontal axis shows time, with the start time of the GI phase of the cell cycle being defined as 0, and the time of each of the S phase and the G2 phase/M phase can be seen. The vertical axis in FIG. 4 shows relative density of an expression amount of the ion channels. It has been found out from this measurement result that the expression amount of the ion channels increases/decreases depending on each phase of the cell cycle. Generally, the expression amount of the ion channels correlates with the reaction of a cell (in this case, potential change of a cell membrane), and therefore, the above measurement result implies that the reaction of the cells changes depending on each phase of the cell cycle. Specifically, in the case of the SK2 channel, reactivity is high in the G1 phase and reactivity lowers in the S phase and the G2 phase/M phase.

As described above, in order to study the correlation (for example, FIG. 4) between the initial states of cells and their reactions by using the conventional method, a large variety of specimens in different cell initial states has to be prepared by the synchronous culture method, which requires enormous labor and time.

SUMMARY OF THE INVENTION

It is an object of the present invention to provide a cell observation device and a cell observation method which can facilitate to study the correlation between initial states of cells and their reactions without using the synchronous culture method.

A cell observation device of the present invention includes an image acquisition unit acquiring an image of a specimen including a plurality of cells; a stimulating unit applying a predetermined stimulation to the plural cells; a determining unit determining initial states of the plural cells from the image which is acquired by the image acquisition unit before the stimulating unit applies the stimulation; a finding unit finding reactions of the plural cells to the stimulation from the image which is acquired by the image acquisition unit after the stimulating unit applies the stimulation; and a generating unit generating information on correlation between the initial states and the reactions of the plural cells.

Preferably, the determining unit determines the initial states of the plural cells according to morphological transformations of the plural cells, referring to a plurality of the images which are acquired by the image acquisition unit in sequence before the stimulating unit applies the stimulation.

Further preferably, the determining unit determines the initial states of the plural cells according to morphological transformations linked with respective cell cycles of the plural cells.

Further preferably, the determining unit determines, as the initial states, states of the plural cells immediately before the stimulating unit applies the stimulation.

Further preferably, the determining unit determines, as the initial states, phase deviations in the cell cycles of the plural cells.

Another cell observation device of the present invention includes an image acquisition unit acquiring an image of a specimen including a plurality of cells; a stimulating unit applying a predetermined stimulation to the plural cells; a calculating unit discriminating mitotic phases of the plural cells according to morphological transformations linked with respective cell cycles of the plural cells, referring to a plurality of the images which are acquired by the image acquisition unit in sequence before the stimulating unit applies the stimulation, to calculate elapsed times from the mitotic phases of the plural cells to an instant at which the stimulating unit applies the stimulation; a finding unit finding reactions of the plural cells to the stimulation from the image which is acquired by the image acquisition unit after the stimulating unit applies the stimulation; and a generating unit generating information on correlation between the elapsed times and the reactions of the plural cells.

Further, a cell observation method of the present invention includes: a first step of acquiring an image of a specimen including a plurality of cells before applying a predetermined stimulation to the plural cells; a second step of applying the stimulation to the plural cells; a third step of acquiring an image of the specimen after the second step, to find reactions of the plural cells to the stimulation from the image; and a fourth step of determining initial states of the plural cells from the image acquired in the first step to generate information on correlation between the initial states and the reactions.

Preferably, in the first step, a plurality of the images are acquired in sequence, and in the fourth step, the initial states of the plural cells are determined according to morphological transformations of the plural cells while the plural images are referred to.

Further preferably, in the fourth step, the initial states of the plural cells are determined according to morphological transformations linked with respective cell cycles of the plural cells.

Further preferably, in the fourth step, states of the plural cells immediately before the stimulation is applied are determined as the initial states.

Further preferably, in the fourth step, phase deviations in the cell cycles of the plural cells are determined as the initial states.

Another cell observation method of the present invention includes a first step of acquiring a plurality of images of a specimen including a plurality of cells in sequence before applying a predetermined stimulation to the plural cells; a second step of applying the stimulation to the plural cells; a third step of acquiring an image of the specimen after the second step, to find reactions of the plural cells to the stimulation from the image; and a fourth step of discriminating mitotic phases of the plural cells according to morphological transformations linked with respective cell cycles of the plural cells, referring to the plural images acquired in the first step, to calculate elapsed times from the mitotic phases of the plural cells to an instant at which the stimulation is applied, and generate information on correlation between the elapsed times and the reactions.

According to the present invention, it is possible to easily study the correlation between initial states of cells and their reactions without using a synchronous culture method.

BRIEF DESCRIPTION OF THE DRAWINGS

The nature, principle, and utility of the invention will become more apparent from the following detailed description when read in conjunction with the accompanying drawings in which like parts are designated by identical reference numbers, in which.

DESCRIPTION OF THE PREFERRED EMBODIMENT

Hereinafter, an embodiment of the present invention will be described in detail with reference to the drawings.

Figure 1:
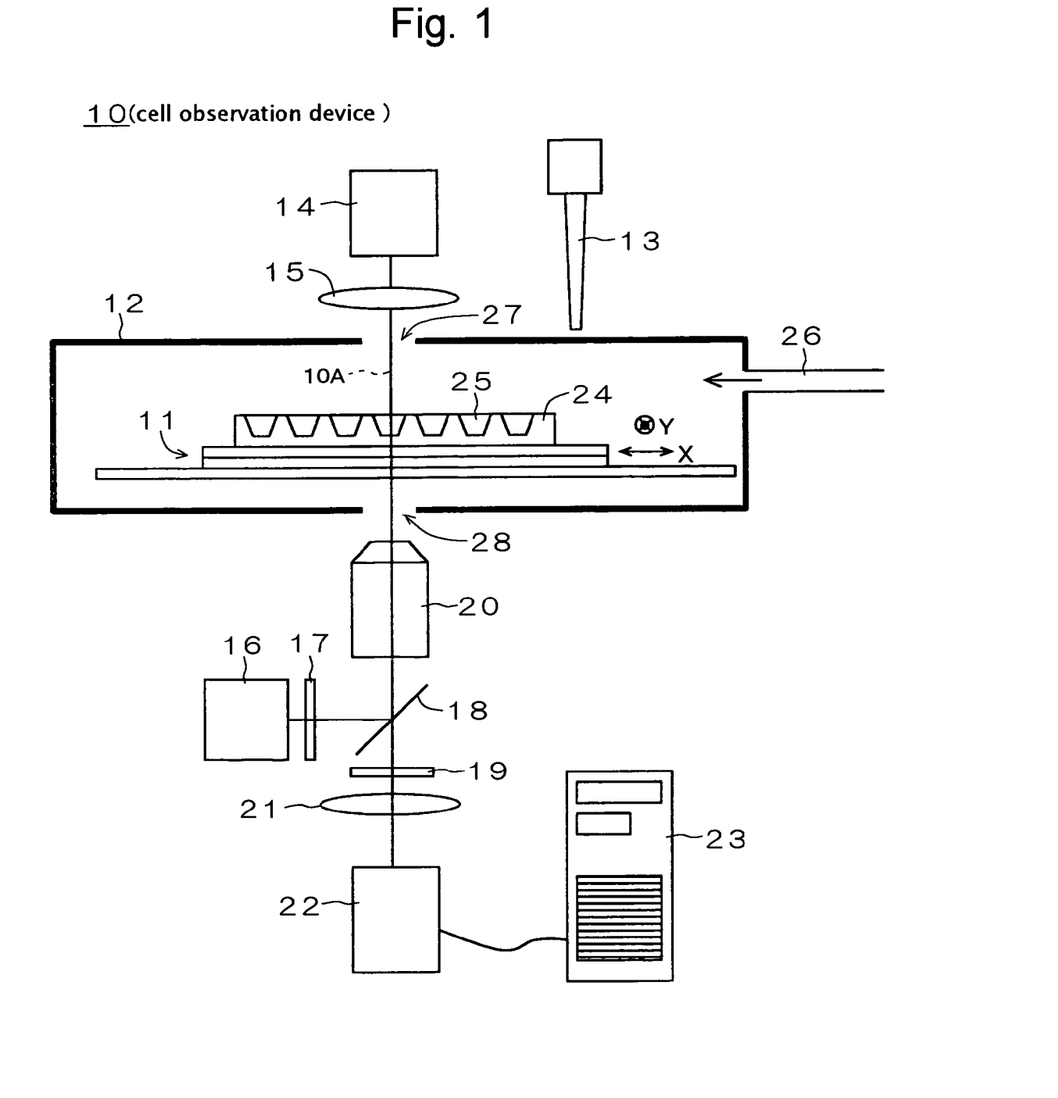
FIG. 1 is a view showing the whole structure of a cell observation device 10.

As shown in FIG. 1, a cell observation device 10 of this embodiment includes a power-driven XY stage 11, a heat-retaining container 12; a pipette device 13, a transillumination unit (14, 15), an epi-illumination unit (16~19), an optical microscope unit (20~22), and a computer 23. A microplate 24 made of, for example, transparent polystyrene and having 96 pieces of wells 25 is placed on the power-driven XY stage 11.

Each of the wells 25 of the microplate 24 contains a specimen including a large number of cells (living cells). The cells are sunk on bottom portions of the wells 25. Here, the cells in the wells 25 are cultured by a typical and simple method and not by a method requiring a complicated work such as a generally known synchronous culture method. Therefore, states (for example, the timing of a mitotic phase (M phase) of a cell cycle) of the large number of cells are not uniform in each of the wells 25.

The power-driven XY stage 11 is a mechanism for moving the microplate 24 in XY directions to position any one of the 96 wells 25 on an observation optical path 10A. The power-driven XY stage 11 is capable of positioning center portions of the wells 25 on the observation optical path 10A in sequence. In the cell observation device 10 of this embodiment, the power-driven XY stage 11 and the microplate 24 are disposed inside the heat-retaining container 12.

The heat-retaining container 12 has a suction port 26 and exhaust ports 27, 28 in a wall made of a heat-insulating material. The suction port 26 is disposed on a side, and the exhaust ports 27, 28 are arranged along the observation optical path 10A on an upper side and a lower side. A sufficient amount of air (temperature 37° C., humidity 100%, carbon dioxide gas 5%) is supplied to the inside of the heat-retaining container 12 through the suction port 26. Therefore, the inside of the heat-retaining container 12 is constantly kept under a fixed condition, even with a slight amount of air escaping from the exhaust ports 27, 28.

Therefore, it is possible to observe the cells in the wells 25 of the microplate 24 under the fixed condition. Note that under the same condition, the length of the cell cycle of an established cultured cell line is constant (for example, 24 hours). In this case, the nonuniformity of the states of the large number of cells in each of the wells 25 is expressed as, for example, phase deviation of the cell cycle or time deviation of a mitotic phase of the cell cycle. The reason for fixing concentration of the carbonic dioxide gas is to keep pH of a solution fixed.

Above the heat-retaining container 12, the pipette device 13 and the transillumination unit (14, 15) are disposed. The pipette device 13 and the transillumination unit (14, 15) are movable in, for example, the X direction by a not-shown stage. Then, the pipette device 13 or the transillumination unit (14, 15) is inserted in the observation optical path 10A. FIG. 1 shows a state in which the transillumination unit (14, 15) is inserted in the observation optical path 10A.

The pipette device 13 is a device which sucks up a prescribed amount of a drug (albuminoid or acetylcholine) from a not-shown drug storage well and thereafter infuses the drug into the wells 25 of the microplate 24. When infusing the drug, the pipette device 13 is inserted in the observation optical path 10A. Then, the drug is infused via the exhaust port 27 of the heat-retaining container 12 into one well 25 positioned on the observation optical path 10A out of the 96 wells 25 of the microplate 24.

The transillumination unit (14, 15) is constituted of a light source 14 and a condenser lens 15, and is inserted in the observation optical path 10A when the cells are observed by transillumination. At this time, illumination light from the light source 14 passes through the condenser lens 15 and the exhaust port 27 of the heat-retaining container 12 and thereafter enters one well 25 positioned on the observation optical path 10A out of the 96 wells 25 of the microplate 24 to illuminate the cells therein. Note that the light transmitting through the cells is led to the optical microscope unit (20~22) after passing through the lower exhaust port 28 of the heat-retaining container 12.

Under the heat-retaining container 12, the epi-illumination unit (16~19) is disposed in addition to the optical microscope unit (20~22). The epi-illumination unit (16~19) is constituted of a light source 16, an excitation filter 17, a dichroic mirror 18, and a fluorescence filter 19 and is inserted in the observation optical path 10A for observation of the cells by epi-illumination.

At this time, illumination light from the light source 16 is led to the observation optical path 10A via the excitation filter 17 and the dichroic mirror 18. After passing through an objective lens 20 of the optical microscope unit (20~22) and the exhaust port 28 of the heat-retaining container 12, it enters one well 25 positioned on the observation optical path 10A out of the 96 wells 25 of the microplate 24 to illuminate the cells therein. In the case of the epi-illumination, fluorescent dye infused into the cells in advance is excited by the illumination light. Note that fluorescence emitted from the fluorescent dye is led to the optical microscope unit (20~22) after passing through the lower exhaust port 28 of the heat-retaining container 12 again.

The optical microscope unit (20~22) is constituted of the objective lens 20, an imaging lens 21, and a camera 22. The light transmitting through the cells in the well 25 by the aforesaid transillumination enters the camera 22 via the objective lens 20 and the imaging lens 21. The fluorescence emitted from the cells (fluorescent dye) in the well 25 by the aforesaid epi-illumination enters the camera 22 via the objective lens 20, the dichroic mirror 18, the fluorescence filter 19, and the imaging lens 21. In any case, magnified images of the cells are formed on an image forming surface of the camera 22. The camera 22 photographs the magnified images to output image data to the computer 23.

The computer 23 acquires an image of the specimen (including a large number of cells) based on the image data outputted from the camera 22 to store the image in a hard disk together with the time when the image is photographed. Note that the computer 23 stores a cell observation program describing the procedure for designating the timing of acquiring the image from the camera 22 and for observing the reactions of the cells caused by the drug based on the acquired image.

Next, operations of the cell observation device 10 of this embodiment will be described. The computer 23 observes the reactions of the cells caused by the drug according to the procedure in the flowchart (Steps S1~S5) shown in FIG. 2 while referring to the cell observation program stored therein.

Figure 2:
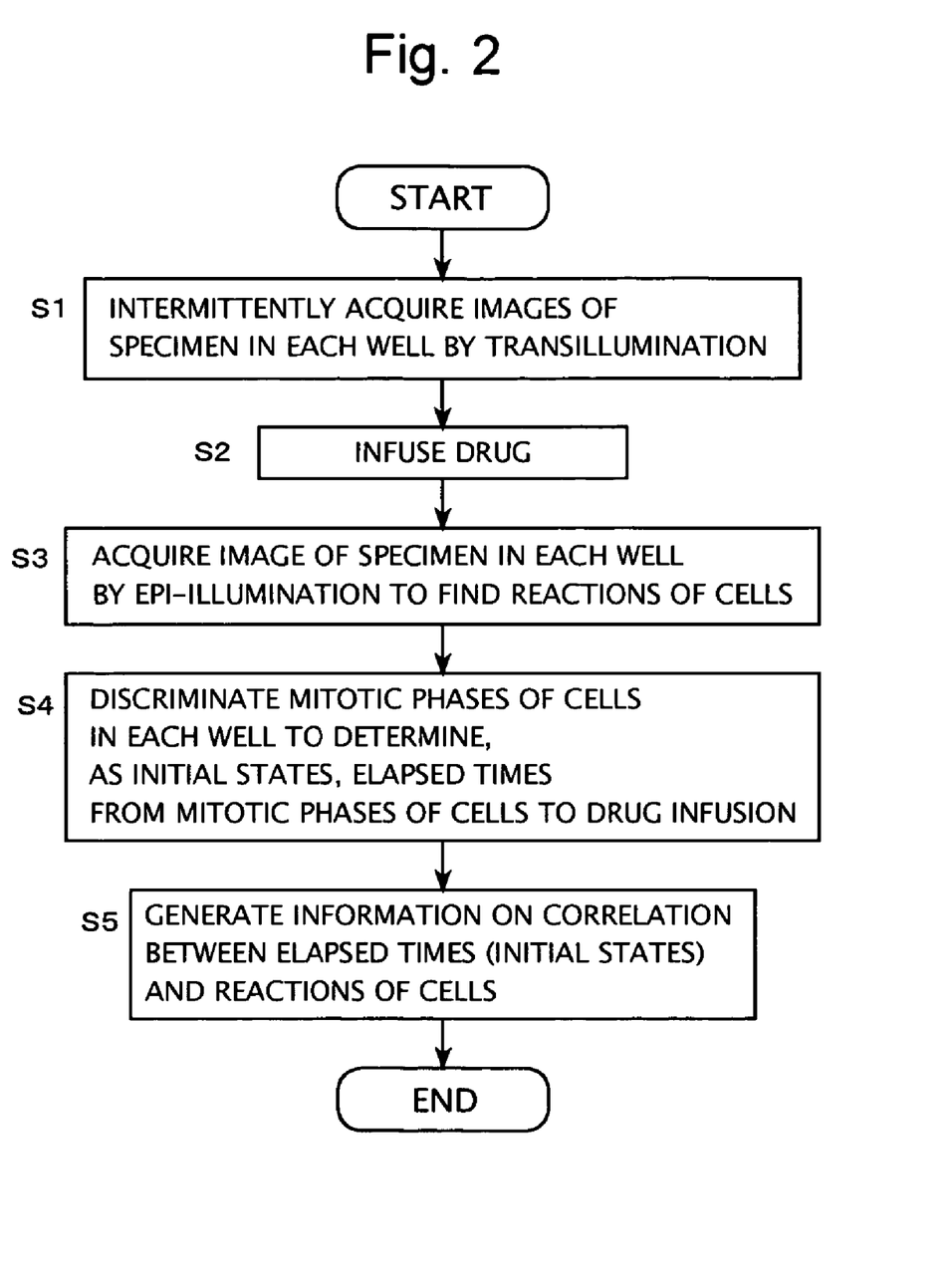
FIG. 2 is a flow chart showing the procedure for observing reactions of cells.

First (Step S1), while the transillumination unit (14, 15) is inserted in the observation optical path 10A, and the pipette device 13 is disposed outside the observation optical path 10A, the computer 23 intermittently acquires the images (corresponding to phase microscope images) of the specimens by the transillumination.

Specifically, the microplate 24 is moved in the XY directions by the power-driven XY stage 11, whereby the center portions of the 96 wells 25 are positioned on the observation optical path 10A in sequence and the images of the specimens in the respective states are acquired. Then, these images are stored in the hard disk together with the time when they are photographed. Further, when the operation of photographing all the wells 25 of the microplate 24 is completed once, the same photographing operation is repeated again in sequence from the first well 25. Repeating the operation of photographing the 96 wells 25 makes it possible to acquire the images of each of the wells 25 in the same field of view intermittently (for example, every 2 minutes).

In this embodiment, the photographing operation at Step S1 is continued for 24 hours, for instance. As a result, for example, 720 pieces of the images in the same field of view are stored, for each of the wells 25, in the hard disk of the computer 23 (photographing interval is 2 minutes). Each of the images is linked with information on the photographing time. Note that 24 hours correspond to the length of a cell cycle. Therefore, each of the large number of cells in the wells 25 mitotically divides once while the photographing operation at Step S1 continues.

As described above, in each of the wells 25, the large number of cells are not in a uniform state, and the timing at which the cells mitotically divide is not uniform either (that is, there is time deviation). The 720 images for each of the wells 25 stored in the hard disk as a result of Step S1 are used for discriminating the mitotic phase (M phase) of each of the large number of cells in the wells 25. The mitotic phase is discriminated at Step S4, which will be described later.

Next (Step S2), the transillumination unit (14, 15) is evacuated from the observation optical path 10A. While the microplate 24 is moved in the XY directions by the power-driven XY stage 111 with the pipette device 13 being inserted in the observation optical path 10, the computer 23 makes the pipette device 13 infuse the drug into each of the 96 wells 25, so that stimulation is applied collectively to the large number of cells in each of the wells 25. The kinds and concentration of the drug may be different among all the wells 25 or the drug of the same kind may be infused into the plural wells 25. Further, the drug infused into each of the wells 25 is not limited to one kind, but a plurality of kinds of drugs may be infused into each of the wells 25 by a plurality of supply operations. The computer 23 records the drug infusion time for each of the wells 25.

Here, the large number of cells in each of the wells 25 (that is, the phase of the cell cycle) are not in a uniform state, therefore, the cells are in different initial states (before the stimulation is applied) from one another due to the collective infusion of the drug as at Step S2. Note that the cells in the different initial states exhibit different reactions to the drug (see FIG. 4). The cells in the same initial state exhibit the same reaction to the drug.

Next (Step S3), while the microplate 24 is moved in the XY directions by the power-driven stage 11, the computer 23 intermittently acquires images (corresponding to fluorescence images) of the specimens by the epi-illumination. Then, the reactions of the large number of cells caused by the drug are found according to these images. The reactions are found in, for example, the following manner: regions of the respective cells are extracted from the fluorescence images and thereafter, luminance changes in the regions of the respective cells are calculated. The reaction to the drug corresponds to an effect of the drug.

Next (Step S4), the computer 23 discriminates the mitotic phase (M phase) of each of the large number of cells in the wells 25 based on the 720 images which are acquired for each of the wells 25 at Step S1, and the elapsed times from the mitotic phases to the drug infusion are calculated. This elapsed time corresponds to the time deviation of the mitotic phase (M phase) of each of the cells, in other words, corresponds to phase deviation in the cell cycle. Further, this can be considered to be the initial state (state before the stimulation is applied) of each of the cells. That is, at Step S4, the elapsed times from the mitotic phases (M phases) of the cells to the drug infusion are determined as the initial states.

Figure 3:
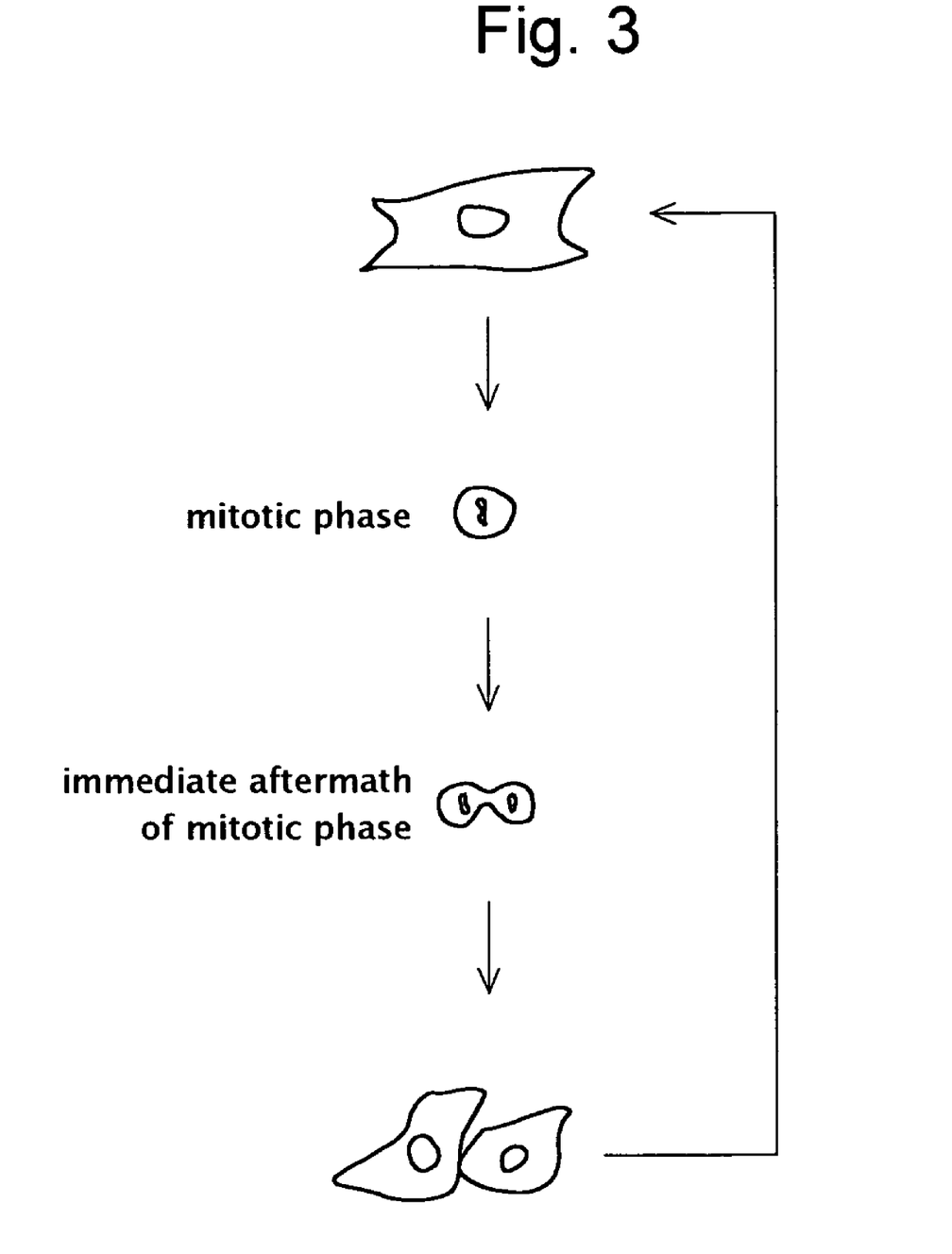
FIG. 3 is a schematic view showing morphological transformation linked with a cell cycle.

Here, image processing for discriminating the mitotic phase (M phase) will be described. Generally, an individual cell exhibits the morphological transformation as shown in FIG. 3 in a cell cycle. Specifically, an individual cell is in an expanded state while not mitotically dividing, but it becomes round to reduce in area at the mitotic phase. Thus, among the morphological transformations (FIG. 3) linked with the cell cycle, one occurring at the mitotic phase is most easily distinguishable from others, so that the mitotic phase of the cell can be easily discriminated by analyzing a feature amount of the area of the cell by image processing software. However, before finding the feature amount of the area of the cell, it is necessary to extract a region of each of the cells from the image.

After finishing the determination of the elapsed times from the mitotic phases (M phases) of the cells to the drug infusion (that is, the initial states of the cells), the computer 23 proceeds to the final Step S5 to generate information on the correlation between the elapsed times (initial states) of the cells and their reactions (effect of the drug) of the cells found at Step S3. This completes the processing for observing the reactions caused by the drug.

As described above, the cell observation device 10 of this embodiment can find the reactions of the individual cells by the simultaneous drug infusion into the large number of cells in a nonuniform state in each of the wells 25, which makes it possible to easily study the correlation between the initial states of the cells and their reactions without using the synchronous culture method.

Further, according to the cell observation device 10 of this embodiment, since the microplate 24 is used as a container for culturing the specimens, it is possible to efficiently observe the reactions of the cells caused by various kinds of drugs at the time of screening in development processes of medicinal products.

MODIFICATION EXAMPLE

In the above-described embodiment, the elapsed times from the mitotic phases of the cells to the drug infusion are determined as the initial states, but the present invention is not limited thereto. The time deviation of the mitotic phase or the phase deviation of the cell cycle of each of the cells may be determined as the initial state. When the phase deviation is determined as the initial state, a phase other than the mitotic phase may be used as a reference. Alternatively, the state of each of the cells immediately before the stimulation (phase of the cell cycle) may be determined as the initial state. This clarifies the correlation between the cell cycle and the effect of the drug.

Further, in the above-described embodiment, in order to discriminate the mitotic phase of the cell, the feature amount of the area of the cell is analyzed, but the present invention is not limited thereto. The mitotic phase may be discriminated based on the morphological transformation (that is, change in shape) of the membrane by acquiring a fluorescence image of the cell membrane by epi-illumination with use of a fluorescent reagent (such as Dipheny-Hexatriene (DPH) which dyes a cell membrane in a specific manner. A phase where the cell membrane is round is the mitotic phase. Also, the cells at the mitotic phase may be identified from the morphological transformation of the cell nucleus by acquiring a fluorescence image of the cell nucleus by epi-illumination with use of a fluorescent reagent (Hoechst 33342) which dyes a cell nucleus in a specific manner. The cell nucleus is oval at interphases (other than the mitotic phase), but at the mitotic phase, it condenses to become small; therefore, it is easy to discriminate the mitotic phase from other phases.

Moreover, in addition to a parameter for the cell cycle (for example, the elapsed time or the like) as described above, the following features may be determined as the initial state (before the stimulation is applied). For example, a calmodulin amount (GFP-marked calmodulin) expressed in each of the cells may be used as an index. Intracellular caspase activated by interaction of Fas ligand and Fas may be detected. The interaction of Fas ligand and Fas occurs due to such a contact with an immune cell to induce apoptosis. Activation of apoptosis cascade may be detected from detection of an increase/decrease of p53 protein. A phenomenon such as a lisosomal disease where abnormality occurs in a specific hydrolytic enzyme in a body may be detected. In this case, a dynamic state of initial endosome imported by endocytosis is imaged by bringing a dyed water-soluble substance into a cell, to know its accumulation in the cell or the like through the observation of fluorescence of the images. In the above, the fluorescence concentration or shape is mainly detected. A change in a bound substance and the ligand may be detected from the detection of spectrum change by FRET (fluorescence energy transfer) or the like, or from the detection of a change in fluorescence life with a time-resolved measurement apparatus.

Further, the reactions of the individual cells include: a change in calcium ion concentration in the cell which is obtained from image information on fluorescent calcium indicator; a change in membrane potential which is obtained from image information on membrane potential sensitive dye; apoptosis, an intracellular distribution change of fluorescence-marked protein kinase, transfer of the cell, and loss of the cell due to death which are obtained from image information on caspase-marked reagent.

Further, in the above-described embodiment, the plural images are intermittently acquired in order to determine the initial states (states before the stimulation is applied) of the cells, but the present invention is not limited thereto. The initial states (states before the stimulation is applied) of the cells may be determined from a single image.

Further, the above-described embodiment has described a case where the drug is infused into each of the cells to apply the stimulation thereto, but the present invention is not limited thereto. The present invention is also applicable to a device that observes the reactions of cells by temperature change stimulation (heat shock protein or the like), mechanical stimulation (expansion/contraction stimulation of cells or the like), light stimulation (visual cell or the like), electric stimulation, or the like.

Further, in the above-described embodiment, the reactions of the cells are observed by the epi-illumination, but the reactions can be observed by the transillumination. In this case, after the stimulation is applied, the pipette device 13 is evacuated from the observation optical path 10A and the transillumination unit (14, 15) is inserted in the observation optical path 10A again.

Moreover, in the above-described embodiment, the number of kinds of reactions to observe is one, but a plurality of kinds of reactions to a stimulation may be extracted from the image information to output information on the correlation between these plural kinds of reactions and the initial state. For example, possible reactions may be a change in intracellular calcium ion concentration which is obtained from image information on the fluorescent calcium indicator and apoptosis which is obtained from the image information of the caspase-marked reagent.

Further, the plural cells do not necessarily mean cells of one kind with different states, but they can be mixed cells of a plurality of kinds (for example, a glia cell and a nerve cell).

Further, the above embodiment has described, as an example, the cell observation device 10 including the transillumination unit (14, 15) and the epi-illumination unit (16~19), but the present invention is not limited to this. The present invention is also applicable to a cell observation device including either one of the transillumination unit (14, 15) and the epi-illumination unit (16~19). Another possible structure may be such that the excitation filter 17, the dichroic mirror 18, and the fluorescence filter 19 in the epi-illumination unit (16~19) are movable in, for example, the X direction by a not-shown stage and are evacuated outside the observation optical path 10A at the time of image acquisition by the transillumination.

Further, in the above-described embodiment, the images acquired before the drug infusion are read at Step S4 in FIG. 2, whereby the initial states of the cells are determined, but the present invention is not limited thereto. The determination timing of the initial states of the cells may be between Step S1 and Step S2.

Further, to keep a fixed condition inside the heat-retaining container 12 in a different manner from one described in the above example, an electric heater or a vapor generator may be provided in the heat-retaining container, thereby control temperature/humidity therein by turning ON/OFF them. Also, to keep a fixed concentration of the carbon dioxide gas in another way, the carbon dioxide gas may be supplied through a solenoid valve and the concentration thereof may be control by opening/closing the solenoid valve.

Further, the exhaust ports 27, 28 of the heat-retaining container are not limited to opening parts, but may be glass windows. In this case, the upper exhaust port 27 is preferably openable/closable. The glass window of the exhaust port 27 is kept closed during the observation with the transillumination, while kept open when the pipette device 13 infuses the drug.

Further, the pipette device for drug infusion is not limited to a device having a single tip but may be a device having a plurality of tips. In this case, a reagent can be infused into the plural wells of the microplate.

Further, to infuse the drug in another way different from that in the above-described example, two pipes may be inserted in the cell culture solution to infuse the culture solution containing the drug from one of the pipes, and suck a superfluous amount of the culture solution from the other. Further, a petri dish may be used as the culture container instead of the microplate 24.

The invention is not limited to the above embodiments and various modifications may be made without departing from the spirit and scope of the invention. Any improvement may be made in part or all of the components.

What is claimed is:

1. A cell observation device comprising:
an image acquisition unit acquiring an image of a specimen including a plurality of cells;
a stimulating unit applying a predetermined stimulation to said plural cells;
a calculating unit discriminating mitotic phases of said plural cells according to morphological transformations linked with respective cell cycles of said plural cells, referring to a plurality of images which are acquired by said image acquisition unit in sequence before said stimulating unit applies the stimulation, to calculate elapsed times from the mitotic phases of said plural cells to an instant at which said stimulating unit applies the stimulation;
a finding unit finding reactions of said plural cells to the stimulation from the image which is acquired by said image acquisition unit after said stimulating unit applies the stimulation; and
a generating unit generating information on correlation between the elapsed times and the reactions of said plural cells.

2. A cell observation method comprising:
a first step of acquiring an image of a specimen including a plurality of cells before applying a predetermined stimulation to said plural cells;
a second step of applying the stimulation to said plural cells;
a third step of acquiring an image of the specimen after the second step, to find reactions of said plural cells to the stimulation from the image; and
a fourth step of determining initial states of said plural cells from the image acquired in the first step to generate information on correlation between the initial states and the reactions.

3. The cell observation method according to claim 2, wherein:
in the first step, a plurality of the images are acquired in sequence; and
in the fourth step, the initial states of said plural cells are determined according to morphological transformations of said plural cells while said plural images are referred to.

4. The cell observation method according to claim 3, wherein
in the fourth step, the initial states of said plural cells are determined according to morphological transformations linked with respective cell cycles of said plural cells.

5. The cell observation method according to claim 3, wherein
in the fourth step, states of said plural cells immediately before the stimulation is applied are determined as the initial states.

6. The cell observation method according to claim 4, wherein
in the fourth step, states of said plural cells immediately before the stimulation is applied are determined as the initial states.

7. The cell observation method according to claim 4, wherein, in the fourth step, phase deviations in the cell cycles of said plural cells are determined as the initial states.

8. A cell observation method comprising:

a first step of acquiring a plurality of images of a specimen including a plurality of cells in sequence before applying a predetermined stimulation to said plural cells;

a second step of applying the stimulation to said plural cells;

a third step of acquiring an image of the specimen after the second step, to find reactions of said plural cells to the stimulation from the image; and a fourth step of discriminating mitotic phases of said plural cells according to morphological transformations linked with respective cell cycles of said plural cells, referring to the plural images acquired in the first step, to calculate elapsed times from the mitotic phases of said plural cells to an instant at which the stimulation is applied, and generate information on correlation between the elapsed times and the reactions.

* * * * *